United States Patent
Schmieding et al.

(10) Patent No.: US 8,852,201 B2
(45) Date of Patent: Oct. 7, 2014

(54) MICROFRACTURE INSTRUMENT

(75) Inventors: Reinhold Schmieding, Naples, FL (US);
Kenneth M. Adams, Naples, FL (US);
Philip S. O'Quinn, Naples, FL (US);
Peter J. Millett, Vail, CO (US)

(73) Assignee: Arthrex, Inc., Naples, FL (US)

( * ) Notice: Subject to any disclaimer, the term of this patent is extended or adjusted under 35 U.S.C. 154(b) by 368 days.

(21) Appl. No.: 12/731,971

(22) Filed: Mar. 25, 2010

(65) Prior Publication Data

US 2010/0249786 A1    Sep. 30, 2010

Related U.S. Application Data

(60) Provisional application No. 61/164,732, filed on Mar. 30, 2009.

(51) Int. Cl.
*A61B 17/16* (2006.01)
*A61B 17/17* (2006.01)
*A61B 17/32* (2006.01)

(52) U.S. Cl.
CPC ......... *A61B 17/1633* (2013.01); *A61B 17/1631* (2013.01); *A61B 17/1675* (2013.01); *A61B 2017/320032* (2013.01); *A61B 17/1642* (2013.01); *A61B 17/32002* (2013.01); *A61B 17/1604* (2013.01)
USPC .............................. 606/96; 606/80

(58) Field of Classification Search
USPC ......... 606/79–85, 86 R, 87–89, 90, 167–173, 606/180, 185
See application file for complete search history.

(56) References Cited

U.S. PATENT DOCUMENTS

| | | | | |
|---|---|---|---|---|
| 4,541,423 A | * | 9/1985 | Barber | 606/80 |
| 5,439,005 A | * | 8/1995 | Vaughn | 600/568 |
| 5,667,509 A | * | 9/1997 | Westin | 606/80 |
| 5,851,208 A | | 12/1998 | Trott | |
| 6,068,642 A | * | 5/2000 | Johnson et al. | 606/180 |

(Continued)

FOREIGN PATENT DOCUMENTS

| | | |
|---|---|---|
| FR | 2 861 575 A1 | 5/2005 |
| WO | WO 2007/084649 A2 | 7/2007 |
| WO | WO 2008/031245 A2 | 3/2008 |
| WO | WO 2009/105880 A1 | 3/2009 |

OTHER PUBLICATIONS

Stryker Subchondral Drill, Stryker Endoscopy, "The Formula for Success," www.stryker.com/steelent/groups/public/documents/web_prod/026211.pdf, Copyright 2007.

(Continued)

*Primary Examiner* — Christopher Beccia
(74) *Attorney, Agent, or Firm* — Dickstein Shapiro LLP

(57) ABSTRACT

A bone drill that includes a shaft with a flexible portion having a proximal end and a distal end and a drill tip coupled to the distal end of the shaft. The bone drill also includes a cannulated sheath with a proximal end and a distal end, the sheath housing a portion of the shaft and having a curved portion at the distal end. The drill tip may also be housed within the curved portion of the sheath. The bone drill may also include a hub with an actuator mechanism, the hub being coupled to the sheath, wherein the actuator mechanism retracts the sheath to cause the drill tip to extend beyond the distal end of the sheath.

18 Claims, 8 Drawing Sheets

(56) References Cited

U.S. PATENT DOCUMENTS

| | | | |
|---|---|---|---|
| 6,312,438 B1* | 11/2001 | Adams | 606/159 |
| 7,318,826 B2* | 1/2008 | Teitelbaum et al. | 606/80 |
| 7,959,634 B2* | 6/2011 | Sennett | 606/79 |
| 8,163,018 B2* | 4/2012 | Trieu | 623/17.11 |
| 2005/0054972 A1* | 3/2005 | Adams et al. | 604/22 |
| 2005/0177168 A1 | 8/2005 | Brunnett et al. | |
| 2005/0203527 A1 | 9/2005 | Carrison et al. | |
| 2005/0261692 A1* | 11/2005 | Carrison et al. | 606/79 |
| 2006/0241630 A1* | 10/2006 | Brunnett et al. | 606/80 |
| 2006/0264957 A1* | 11/2006 | Cragg et al. | 606/80 |
| 2008/0114365 A1* | 5/2008 | Sasing et al. | 606/80 |
| 2008/0249481 A1* | 10/2008 | Crainich et al. | 604/264 |

OTHER PUBLICATIONS

Chen, Hongmei et al., "Drilling and Microfracture Lead to Different Bone Structure and Necrosis during Bone-Marrow Stimulation for Cartilage Repair," Journal of Orthopaedic Research, Nov. 2009, pp. 1432-1438.

* cited by examiner

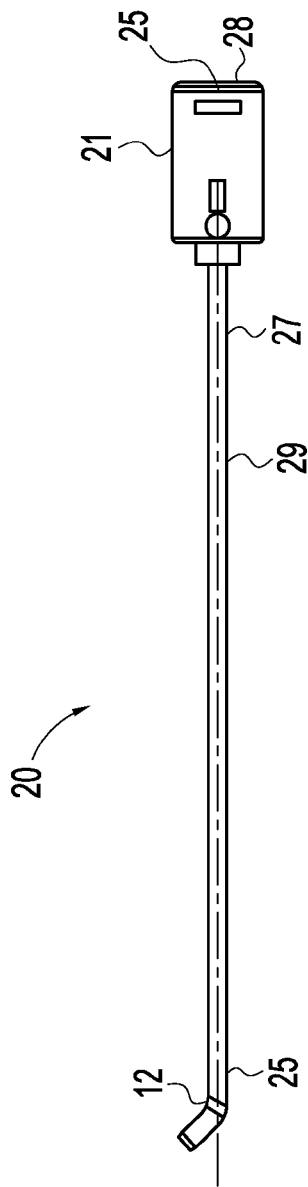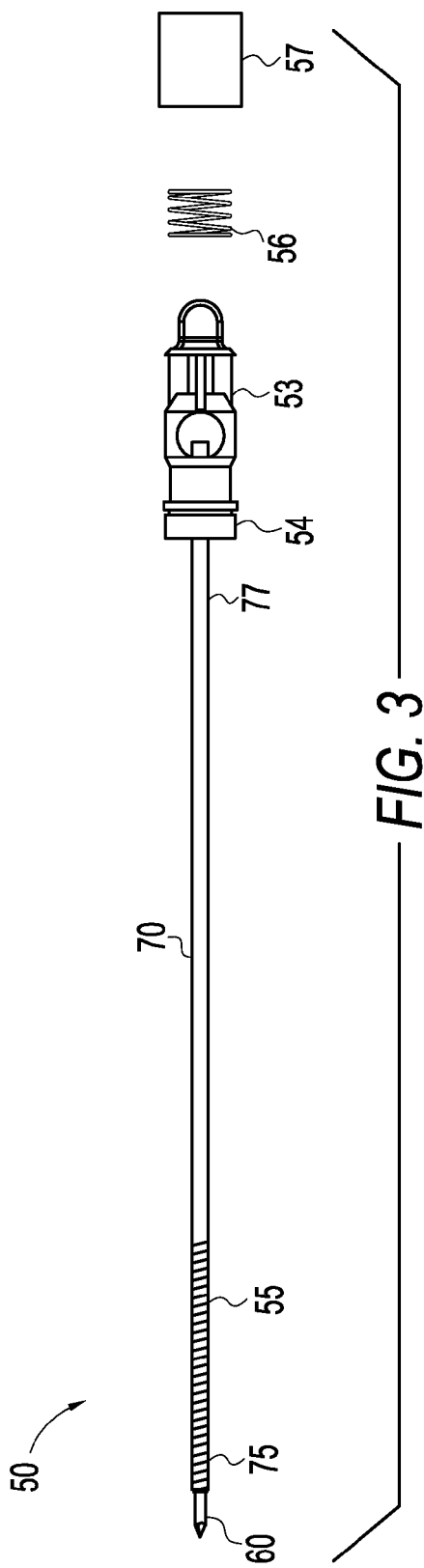

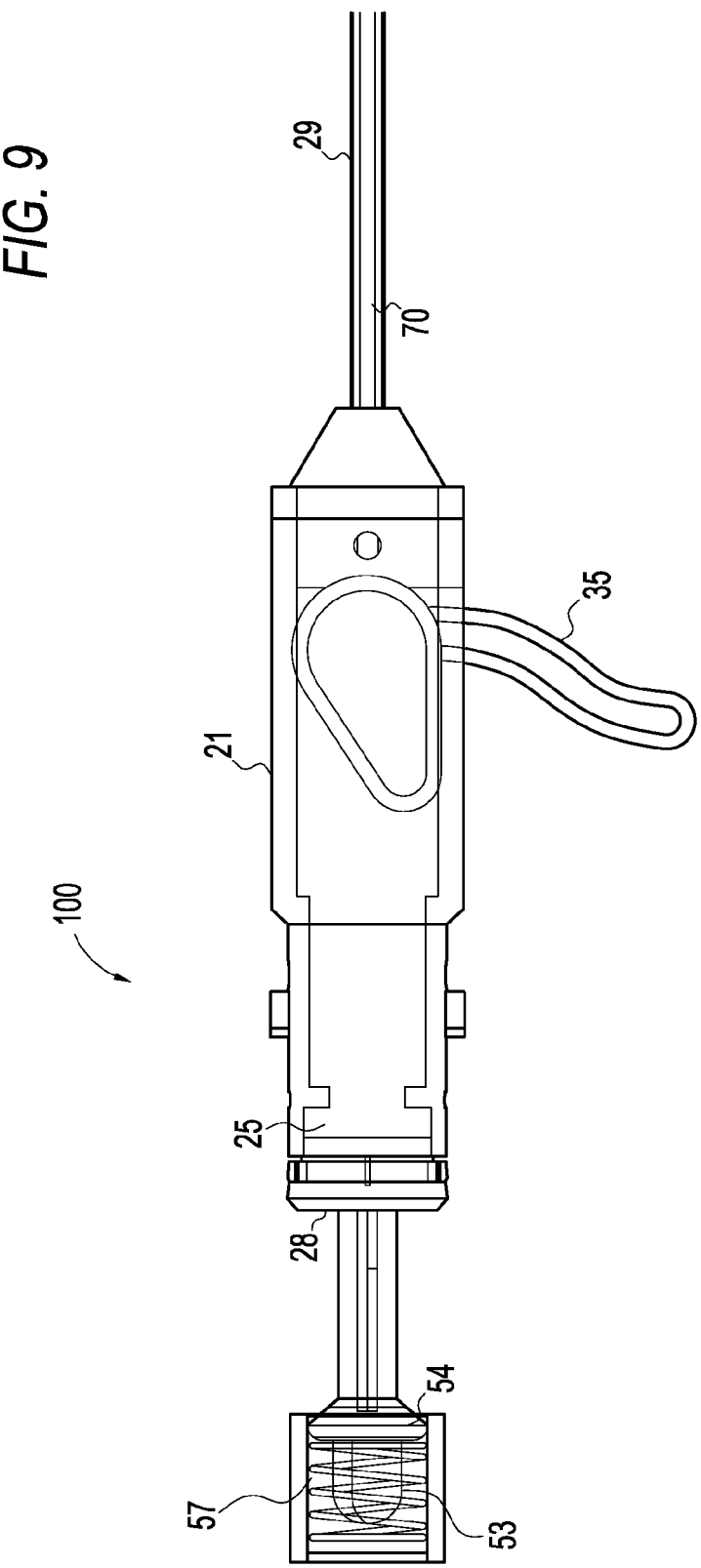

MICROFRACTURE INSTRUMENT

CROSS-REFERENCE TO RELATED APPLICATIONS

This application claims the benefit of U.S. Provisional Application No. 61/164,732, filed Mar. 30, 2009, the entire disclosure of which is incorporated by reference herein.

FIELD OF THE INVENTION

The present invention is directed to surgical instruments and, more particularly, to a device for treating chondral defects of the knee.

BACKGROUND OF THE INVENTION

Treatment of articular cartilage defects is typically accomplished by the microfracture procedure. This procedure is performed arthroscopically. Although articular cartilage defects may occur in any joint, the microfracture procedure is typically performed in the knee or shoulder. The surgeon visually assesses the defect and performs the procedure using special instruments that are inserted through small incisions around the joint. Unstable and loose cartilage is removed from the exposed bone so that there is a stable edge of cartilage surrounding the defect. Multiple holes (also called microfractures) are then made in the exposed bone about 3 to 4 mm apart. Bone marrow cells and blood from the holes combine to form a "super clot" that completely covers the damaged area. This marrow-rich clot is the basis for the new tissue formation. The microfracture technique produces a rough bone surface to which the clot adheres more easily. This clot eventually matures into firm repair tissue that becomes smooth and durable.

The instruments currently used to make the microfractures are manual instruments such as curved picks and/or nitinol wires and guides. One powered option is a subchondral drill which is a straight drill covered by an outer sheath. The outer sheath covers the drill tip until it contacts bone and then the drill tip advances axially into the bone. The manual instruments are undesirable in that they typically require two hands to use since a mallet is used to drive the instruments into the bone. In addition, the impact loading of the mallet may cause the pick to slide or gouge the target site rather than puncture the site perpendicular to the axis of the trocar tip. The straight drill power instrument does not provide adequate accessibility or visibility to the site which is typically in a joint space.

An instrument that can form the microfractures quickly and at pre-determined angles with repeatability is needed. Also needed is an instrument that allows the surgeon to quickly place the microfractures in the desired position using only one instrument attached to power, and with improved accessibility and visibility to the site.

SUMMARY OF THE INVENTION

The present invention provides an instrument for forming microfractures quickly and at pre-determined angles. The instrument takes less time and replaces the use of multiple manual instruments. The instrument attaches to a power system such as that used for shavers and burrs to quickly drill small diameter holes at pre-determined angles into bone. The instrument is provided with a flexible trocar tip and a curved outer sheath. The shaft of the flexible trocar tip connects to the hand piece. The outer sheath protects the sharp trocar tip during insertion and is retracted once positioned to expose the sharp trocar tip. The instrument allows the surgeon to quickly place the microfractures in the desired position using only one instrument attached to power.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 2 illustrates a side view of the outer assembly of the microfracture instrument of FIG. 1;

FIG. 3 illustrates a side view of the inner assembly of the microfracture instrument of FIG. 1 attached to the inner hub;

FIG. 7 illustrates a side view of the outer sheath of the outer assembly of FIG. 2;

FIG. 7(a) illustrates an end view of the outer sheath of the outer assembly of FIG. 7;

FIG. 9 illustrates a transparent side view of the microfracture instrument of FIG. 1;

DETAILED DESCRIPTION OF THE PREFERRED EMBODIMENTS

Figure 1:
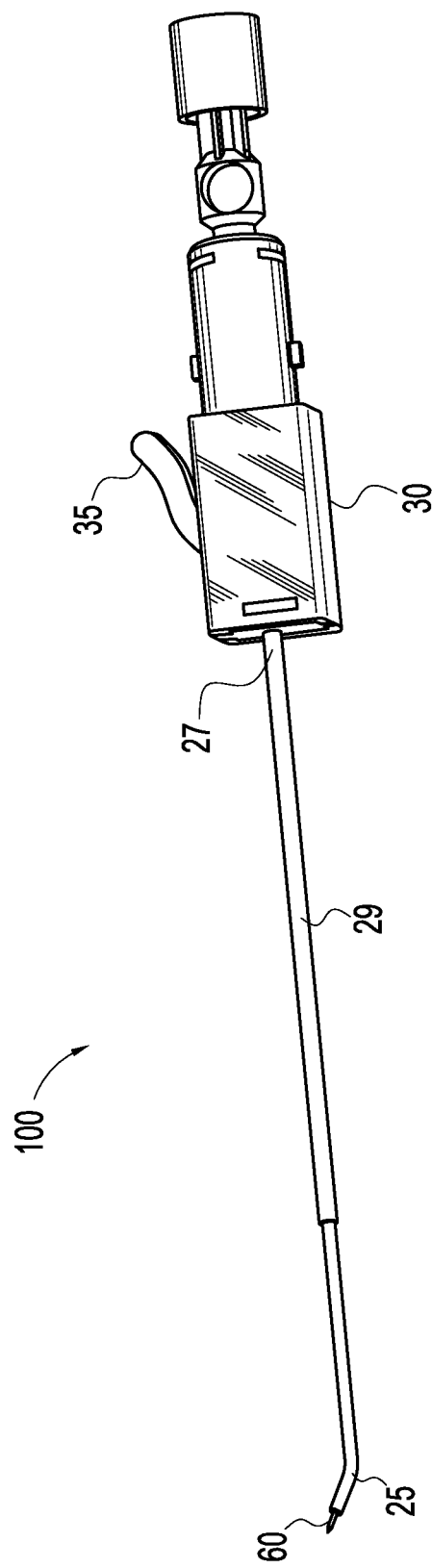
FIG. 1 illustrates a side view of a microfracture instrument of the present invention with the trocar tip exposed.
Figure 1A:
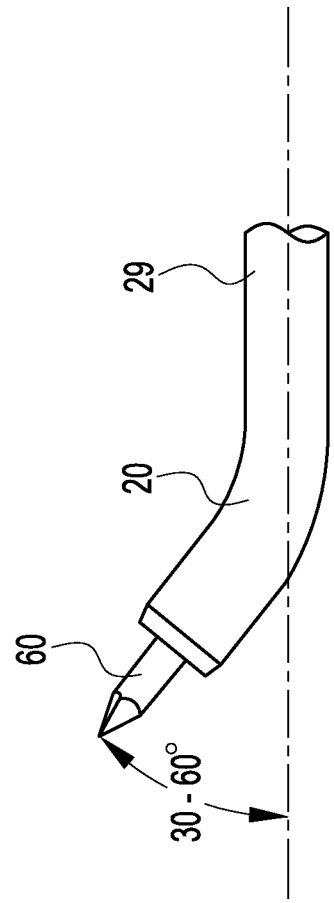
FIG. 1(a) illustrates an enlarged view of the trocar tip of the microfracture instrument of FIG. 1.
Figure 4:
FIG. 4 illustrates a side view of the inner assembly of FIG. 3 (without the inner hub)
Figure 5:
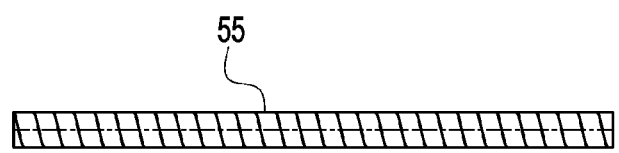
FIG. 5 illustrates a side view of the flex coil of the inner assembly of FIG. 3.
Figure 5A:
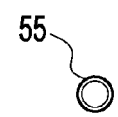
FIG. 5(a) illustrates an end view of the flex coil of the inner assembly of FIG. 5.
Figure 6:
FIG. 6 illustrates a side view of the drive tube of the inner assembly of FIG. 3.
Figure 6A:
FIG. 6(a) illustrates an end view of the drive tube of the inner assembly of FIG. 6.

The following description is provided to enable any person skilled in the art to make and use the invention and sets forth the best modes contemplated by the inventors of carrying out their invention. Various modifications, however, will remain readily apparent to those skilled in the art.

The present invention provides a microfracture instrument for forming small diameter holes in bone. The microfracture instrument of the present invention is designed to attach to a power system (such as one used for shavers and burrs, for example) to quickly drill small diameter holes at pre-determined angles into bone. The microfracture instrument is provided with a flexible trocar tip and a curved outer sheath. The shaft of the flexible trocar tip connects to the hand piece. The outer sheath protects the sharp trocar tip during insertion and is retracted once positioned to expose the sharp trocar tip. The instrument allows the surgeon to quickly place the microfractures at the desired position using only one instrument attached to power.

The present invention also provides a method of drilling a hole in a bone by inter alia: providing a shaft with a flexible end, the flexible end being coupled to a drill tip; providing a cannulated sheath with a distal end and a proximal end, the distal end of the sheath being curved and housing the drill tip; and retracting the sheath to cause the drill tip to extend beyond the distal end of the sheath.

Referring now to the drawings, where like elements are designated by like reference numerals, FIGS. 1-12 illustrate an exemplary microfracture instrument 100 of the present invention for forming small diameter holes in bone.

The microfracture instrument 100 of the present invention may be employed during a microfracture procedure, which is conducted arthroscopically to treat articular cartilage defects, for example, chondral defects of the knee. The surgeon visually assesses the defect and performs the procedure using special instruments that are inserted through small incisions on the knee. After assessing the cartilage damage, any unstable or loose cartilage is removed from the exposed bone, leaving a stable edge of cartilage around the defect.

Multiple holes (or microfractures) are then made in the exposed bone about 3 to 4 mm apart. Bone marrow cells and blood from the holes combine to form a "super clot" that completely covers the damaged area. This marrow-rich clot is the basis for the new tissue formation. The microfracture technique produces a rough bone surface that the clot adheres to more easily. This clot eventually matures into firm repair tissue that becomes smooth and durable. Similar microfracture procedures are used in other surgical sites to treat similar bone and cartilage defects, such as Hill-Sachs lesions in the shoulder.

As illustrated in FIGS. 1-12, microfracture instrument 100 of the present invention includes an outer assembly 20 and an inner assembly 50. The microfracture instrument 100 connects to a shaver hand piece (not shown) for power.

As illustrated in more detail in FIGS. 2 and 7, the outer assembly 20 includes an outer sheath 29 having a cannulated shaft provided with a distal 25 and proximal end 27. In an exemplary embodiment, the distal end 25 of the sheath 29 is curved (FIG. 1). The angle of curvature may be between about 5 to about 80 degrees, preferably between about 30 to about 60 degrees. As also illustrated in FIG. 2, the outer assembly 20 also includes an outer hub 21 with a retaining ring 25. The outer hub 21 is designed to receive the inner assembly 50 through a most proximal opening 28 (FIG. 9).

The outer hub 21 is also provided with an actuator mechanism 35 (FIG. 9) for moving the sheath 29 along a longitudinal axis of the microfracture instrument 100. The proximal end 27 of the sheath 29 connects to the actuator mechanism 35. In an exemplary embodiment only, the actuator mechanism 35 is a lever, but one skilled in the art will recognize alternate embodiments such as a button or a ratchet for moving the shaft along the longitudinal axis.

Figure 12:
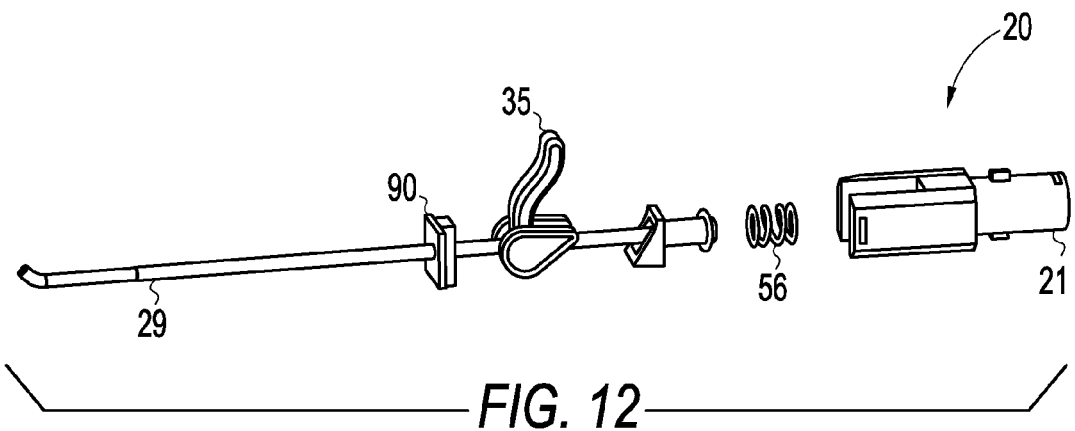
FIG. 12 illustrates a side view of various parts of the microfracture instrument of FIG. 1.

The outer assembly 20 is further illustrated in more detail in FIG. 12. The outer assembly 20 includes the outer sheath 29, the actuator 35, the spring 56, the outer hub 21, and a cap 90. The cap 90 is shown in greater detail in FIG. 11.

Figure 8:
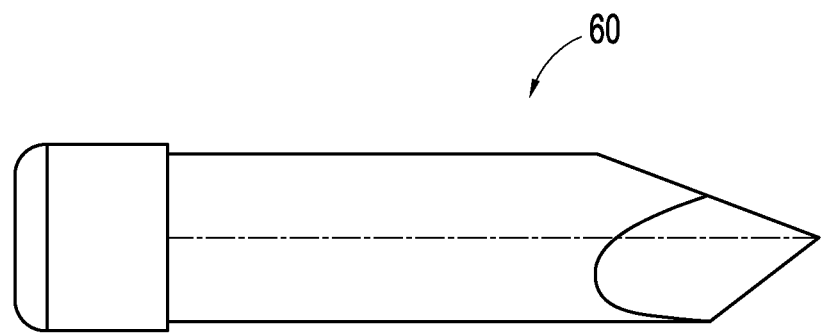
FIG. 8 illustrates a side view of the trocar tip of the inner assembly of FIG. 3.
Figure 8A:
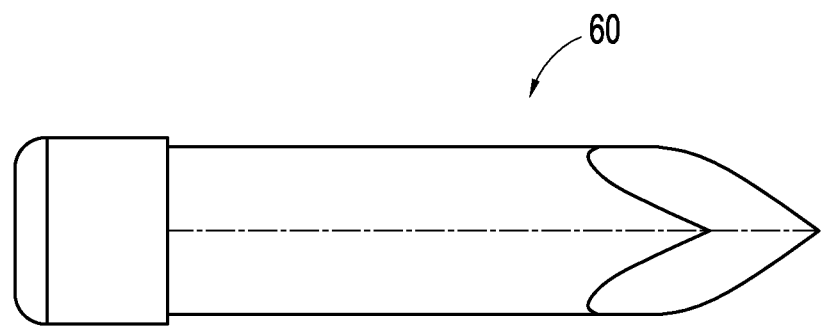
FIG. 8(a) illustrates a side view of the trocar tip of FIG. 8, but rotated for about 90 degrees.
Figure 10:
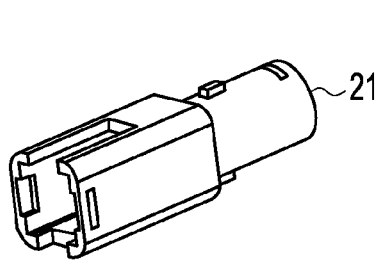
FIGS. 10 and 10(a) illustrate different views of the outer hub of the microfracture instrument of FIG. 1.
Figure 10A:
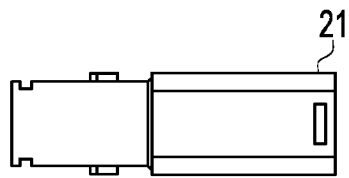
Figure 11:
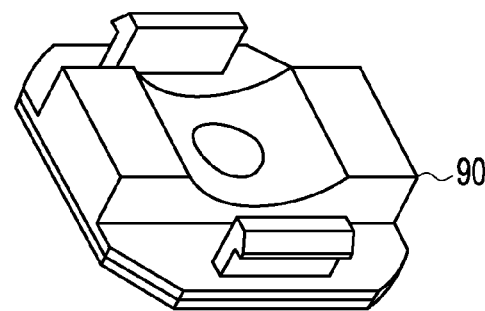
FIG. 11 illustrates a side view of the molded cap of the microfracture instrument of FIG. 1.

The inner assembly 50 of the microfracture instrument 100 is illustrated in more detail in FIGS. 3-6 and 8. As illustrated in FIG. 3, inner assembly 50 comprises an inner shaft 70 extending from a proximal end 77 to a distal end 75. The distal end 75 of the inner shaft houses a drill tip or trocar tip 60 for creating small diameter holes in bone. Details of trocar tip 60 are illustrated in FIG. 8, although the drill tip could have other geometries and could be fluted or in the form of a bur, for example. As shown in FIG. 3, the inner assembly 50 further includes an inner hub 53, a thrust washer 54, a spring 56, and a corresponding spring retainer 57.

The proximal end 77 of the inner shaft 70 connects to the inner hub 53 (FIG. 3). In turn, inner hub 53 connects to a shaver hand piece for power to drive the trocar tip 60 into bone. The inner shaft 70 has a flexible portion 55 (a flex coil 55 shown in FIG. 5) allowing the inner assembly 50 to conform to the curvature of the distal end 25 of the outer sheath 29 of the outer assembly 20.

When inserted into the joint space, the outer sheath 29 of the microfracture instrument 100 covers the trocar tip 60 protecting the surrounding anatomy. Once the desired location for creating the microfracture is located through the scope, the surgeon can manipulate the lever/actuator 35 to retract the sheath 29 thereby exposing the trocar tip 60. Once the tip 60 is exposed, the surgeon may turn on the power to create the hole in the bone. This technique provides the surgeon with more accessibility to the bone in the joint space due to the curvature of the outer sheath. The profile of the instrument 100 is also reduced since the tip is retracted during insertion resulting in better placement of the instrument in the joint space. An additional safety feature is the protection of the surrounding anatomy from an exposed tip during insertion of the instrument prior to drilling.

Figure 13:
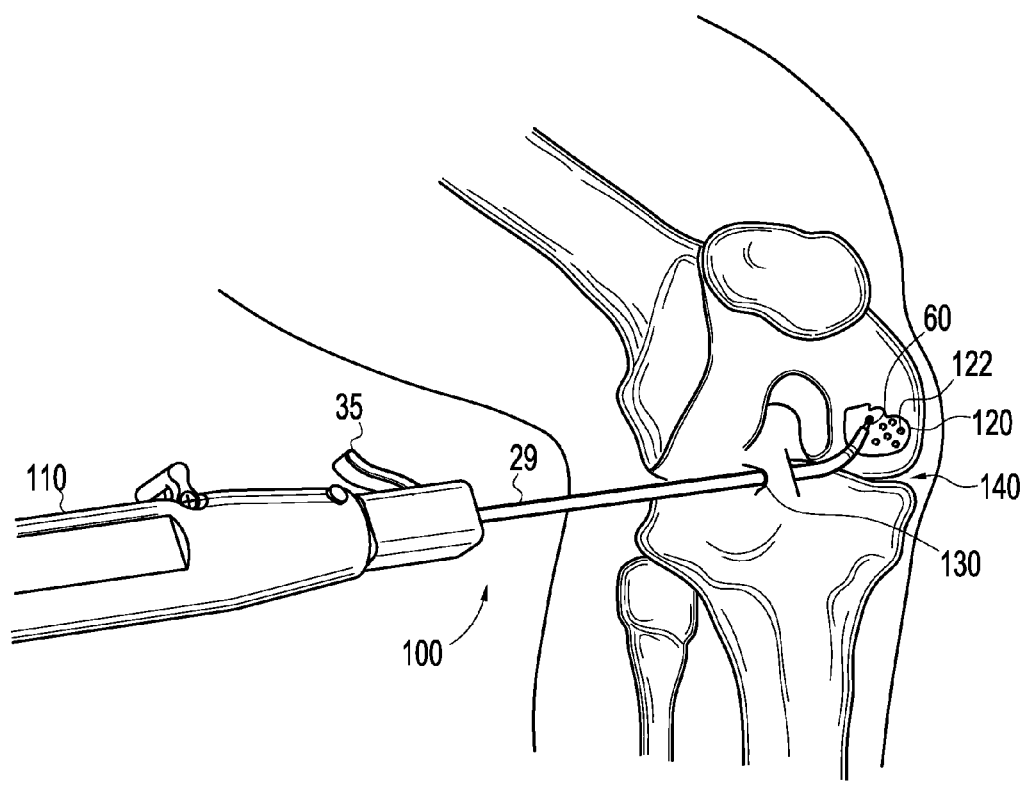
FIG. 13 illustrates a method of using the microfracture instrument of FIG. 1.

An exemplary method of preparation and insertion of the instrument 100 of the present invention (shown in use in FIG. 13) is detailed below with reference to specific steps:

The damaged articular cartilage area is prepared in the standard fashion.

The instrument 100 is then attached to a handpiece 110 with the trocar tip 60 retracted safely within the outer sheath 29.

Next, the instrument 100 is passed into the joint space 140 through a cannula or percutaneously 130.

The actuator mechanism 35 is then actuated to laterally move outer sheath 29, thereby exposing the trocar tip 60 so that the trocar tip 60 extends out of the outer sheath 29.

Next, the trocar tip 60 is placed in the appropriate location for forming a hole 122.

The handpiece 110 is energized to rotate the trocar tip 60 and the trocar tip 60 is pushed into bone 120 until the outer sheath 29 contacts bone 120, thereby forming a 1.5 mm hole 122 approximately 3 mm deep in the bone 120.

The instrument 100 is retracted while the handpiece 110 is still energized and the trocar tip 60 is rotating.

The above steps are repeated as needed on different locations of the damaged cartilage as needed until the microdrilling procedure is complete.

Thereafter, the trocar tip 60 is retracted by raising the actuator 35 so that the trocar tip 60 is housed in outer sheath 29 and the instrument 100 is removed from the joint space.

The instrument 100 is also an ideal tool for marking the femoral tunnel location in ACL reconstructive procedures by following the above steps and using the trocar tip 60 to mark a tunnel location within the femoral notch. Using the laser mark 12 (shown in FIG. 2) on the sheath 29, the approximate tunnel location can be determined through the medial portal by placing the end of the sheath 29 at the over-top-position.

The trailing edge of the laser mark 12, which is the edge of the mark 12 farthest from the end of the sheath 29 from which the trocar tip 60 extends, is used to reference the center of the tunnel in a Single Bundle ACL technique.

The leading edge of the laser mark 12, which is the edge of the mark 12 nearest to the end of the sheath 29 from which the trocar tip 60 extends, is used to reference the center of the posterior tunnel in a Double Bundle ACL technique. After marking its position, the same measurement method is used to reference the center of the anterior tunnel referenced from the previously marked posterior tunnel position. Further, the leading and trailing edges of the laser mark 12 may be used to measure osteochondral defects.

In one embodiment, the laser mark 12 is 2 mm wide, the leading edge is 5 mm from the end of the sheath 29 from which the trocar tip 60 extends and the trailing edge is 7 mm from the end of the sheath 29 from which the trocar tip 60 extends. In other embodiments, different widths and distances may be used.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed as new and desired to be protected by Letters Patent of the United States is:

1. A bone drill comprising:
   an inner assembly comprising a shaft with a flexible portion having a proximal end and a distal end; a drill tip coupled to the distal end of the shaft, the shaft housing the drill tip; and an inner hub for connecting the bone drill to a power system; and
   an outer assembly including a cannulated sheath with a proximal end and a distal end, the sheath having a curved portion at the distal end and housing a portion of the shaft and the drill tip, the cannulated sheath covering the drill tip, the drill tip being housed within the curved portion of the cannulated sheath, the cannulated sheath being retractable to expose the drill tip and to subsequently allow drilling of a bone with the exposed drill tip;
   an actuator mechanism for moving the cannulated sheath along a longitudinal axis of the shaft, the actuator mechanism retracting the sheath so that the drill tip extends beyond the distal end of the sheath; and
   a power system coupled to the shaft to drive the drill tip into bone.

2. The bone drill of claim 1, wherein the flexible portion of the shaft is housed in the curved portion of the sheath.

3. The bone drill of claim 1, further comprising a hub with the actuator mechanism, the hub being coupled to the sheath.

4. The bone drill of claim 1, wherein the flexible portion of the shaft is at the distal end of the shaft.

5. The bone drill of claim 1, wherein the drill tip is a trocar tip.

6. The bone drill of claim 1, wherein the power system rotates the shaft.

7. The bone drill of claim 1, wherein a curvature of the curved portion of the sheath ranges between about 5° to about 80°.

8. The bone drill of claim 1, wherein a curvature of the curved portion of the sheath ranges between about 30° to about 60°.

9. A method of drilling a hole in a bone comprising:
   providing a shaft with a flexible end, the flexible end being coupled to a drill tip, the shaft housing the drill tip;
   providing a cannulated sheath with a distal end and a proximal end, the distal end of the sheath being curved and housing the drill tip, the cannulated sheath covering the drill tip, the drill tip being housed within the curved portion of the cannulated sheath;
   retracting the sheath so that the drill tip is exposed and extends beyond the distal end of the sheath; and
   after the step of exposing the drill tip, drilling the hole in the bone with the exposed drill tip.

10. The method of claim 9, further comprising rotating the drill tip to drill the hole in the bone.

11. The method of claim 10, further comprising pushing the drill tip into the bone until the sheath contacts the bone.

12. The method of claim 9, further comprising providing a hub with an actuator mechanism coupled to the sheath.

13. The method of claim 12, wherein the actuator mechanism displaces the sheath so that the drill tip extends beyond the distal end of the sheath.

14. The method of claim 9, wherein a curvature of the curved portion of the sheath ranges between about 5° to about 80°.

15. The method of claim 9, wherein a curvature of the curved portion of the sheath ranges between about 30° to about 60°.

16. The method of claim 9, wherein the flexible end of the shaft is housed within the curved portion of the sheath.

17. The bone drill of claim 1, wherein the sheath is provided at the distal end with laser marks for marking a tunnel location, for referencing a center of a tunnel, or for measuring ostheochondral defects.

18. The method of claim 9, wherein the sheath is provided at the distal end with laser marks for marking a location of the hole, or for referencing a center of the hole.

* * * * *